United States Patent [19]
Mitrani

[11] Patent Number: 5,888,720
[45] Date of Patent: Mar. 30, 1999

[54] IN VITRO MICRO-ORGANS

[75] Inventor: Eduardo Mitrani, Newton, Mass.

[73] Assignee: Yissum Research and Development Company of The Hebrew University of Jerusalem, Jerusalem, Israel

[21] Appl. No.: 341,409

[22] Filed: Nov. 16, 1994

Related U.S. Application Data

[63] Continuation-in-part of Ser. No. 153,766, Nov. 17, 1993, abandoned, and a continuation-in-part of Ser. No. 967,262, Oct. 27, 1992, Pat. No. 5,387,576.

[51] Int. Cl.$^6$ ................................................. A01N 1/02
[52] U.S. Cl. ........................... 435/1.1; 435/347; 435/373; 435/374
[58] Field of Search ................................ 435/1.1, 240.2, 435/347, 373, 374

[56] References Cited

U.S. PATENT DOCUMENTS

| | | | |
|---|---|---|---|
| 3,734,851 | 5/1973 | Matsumura | 210/22 |
| 4,533,635 | 8/1985 | Guedon et al. | 435/240 |
| 4,835,102 | 5/1989 | Bell et al. | 435/29 |
| 4,888,291 | 12/1989 | Barrandon et al. | 435/240.241 |
| 4,940,666 | 7/1990 | Boyce et al. | 435/240.2 |
| 5,032,508 | 7/1991 | Naughton et al. | 435/32 |
| 5,282,859 | 2/1994 | Eisenberg | 623/11 |
| 5,292,655 | 3/1994 | Wille | 435/240.2 |

FOREIGN PATENT DOCUMENTS

| | | |
|---|---|---|
| 0 271 211 | 11/1987 | European Pat. Off. . |
| 0 361 957 | 9/1989 | European Pat. Off. . |
| 0 418 035 | 9/1990 | European Pat. Off. . |
| WO 91/12334 | 1/1991 | WIPO . |

OTHER PUBLICATIONS

Agren et al, Diabetes 29 (Suppl. 1): 64–69, 1980.
Gerlach, Jorg, C., *Acute Liver Failure*, Edited by William M. Lee & Roger William, Cambridge University Press (1991), Chapter 19, pp. 245–254.
Granov, A.M. et al. *Vestn. Khir* (1976) vol. 116: 106–109. Abstract.
Eisman & Soyer, *Transplantation Proceedings*, (1971), vol. 111, No. 9, pp. 1519–1524.
Soyer, T., et al, *The American Journal of Surgery*, (1973), vol. 126, pp. 20–24.
Soyer, T., et al, *Surgical Forum*, (1971), vol. 23, pp. 346–349.
1951 Pinkus, *J. Invest. Dermatol.* 16:383–386.
1975 Rheinwald et al., *Cell* 6:331–337.
1983 Boisseau et al., *J. Dermatol. Sci.* 3:111–120.
1983 Boyce et al., *J. Invest. Dermatol.* 81:33–34.
1985 Kao et al., *Toxicol. and App. Pharmacol.* 81:502–516.
1986 Bell et al., "Testskin: A Hybrid Organism Covered by a Living Human Skin Equivalent Designed for Toxicity and Other Testing," symposium entitled Progress in In Vitro Toxicology.
1987 Freshney, *Culture of Animal Cells: A Manual of Basic Technique*, 2nd ed., New York:Alan R. Lies, Inc., pp. 297–307.
Bell et al., *Alternative Methods in Toxicology*, Goldberg, ed., vol. 6, pp. 15–25.
1989 Goldberg ed., *Alternative Methods in Toxicology*, vol. 7, pp. v–vi.
1990 Choi et al., *Cell Reg.* 1:791–809.
1990 Kondo et al., *J. Invest. Derm.* 95:397–402.
1991 Parenteau et al., *J. Cell. Biochem.* 45:245–251.
1991 Li et al., *Proc. Natl. Acad. Sci. USA*, 88:1908–1912.
1991 Sugihara et al., *In Vitro Cell. Dev. Biol.* 27A:142–146.
1992 Philpott et al., *Brit. J. Dermatol.* 127:600–607.
1992 Coulomb et al., *Pathol. Biol. Paris*, 40:139–146.
1992 Gurdon, *Cell* 68:185–199.
1992 Reynolds et al., *Development* 115:587–593.
1993 Varani et al., *Am. J. Pathol.* 142:1813–1822.
1994 Watson et al., *Brit. J. Dermatol.* 131:827–835.

*Primary Examiner*—Francisco Prats
*Attorney, Agent, or Firm*—Bromberg & Sunstein LLP

[57] ABSTRACT

A micro-organ culture is provided that includes a nutrient medium in a culture vessel, the vessel containing an oxygen concentration not substantially greater than that in the atmosphere and a population of non-fetal animal cells disposed in the nutrient medium for greater than 24 hours. The population of cells is derived from an organ which has an in vivo structure including an epithelial tissue and an adjacent stroma. The population of cells consists of a plurality of cell types, the population including both stromal and epithelial tissues of the in vivo tissue structure. Furthermore, the population of cells has a volume described by a first, second and third dimension such that at least one dimension is no greater than 0.45 mm. The stromal and epithelial tissues are preserved in the nutrient medium devoid of an internally disposed synthetic support structure or sandwich structure.

20 Claims, 14 Drawing Sheets

FIG. 2C-A
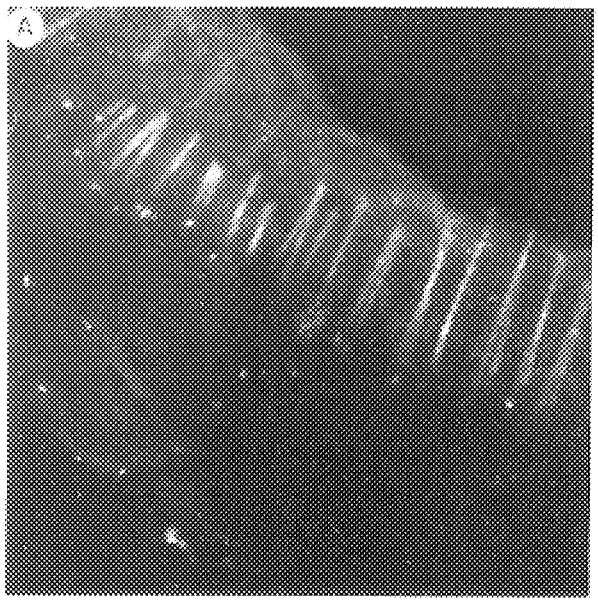
FIG. 2C-B
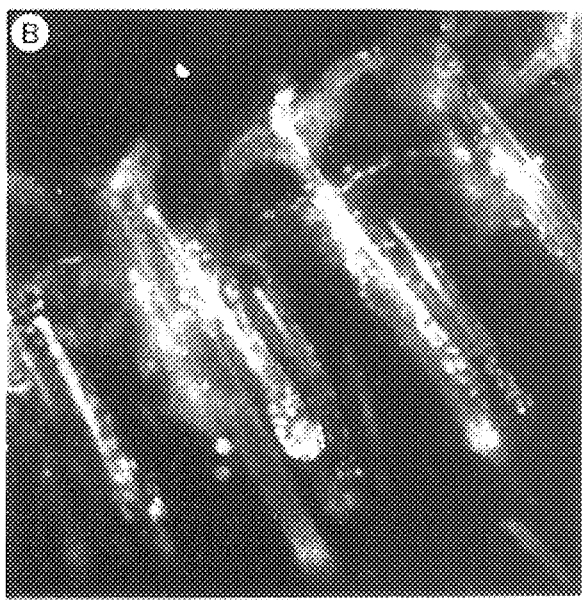
FIG. 2C-C
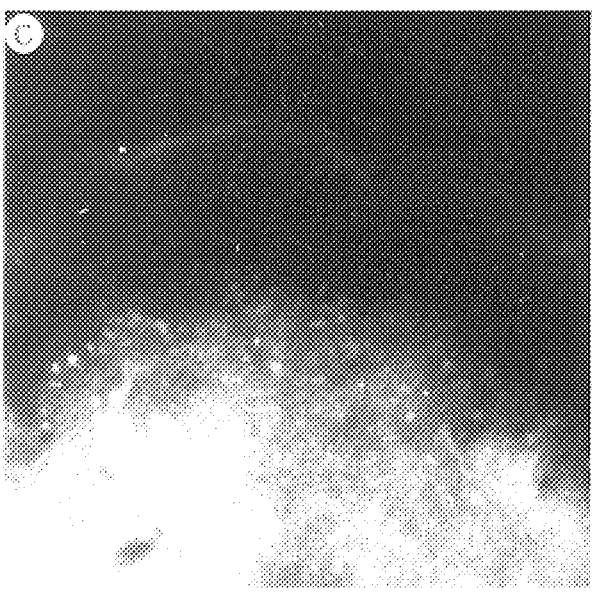
FIG. 2C-D
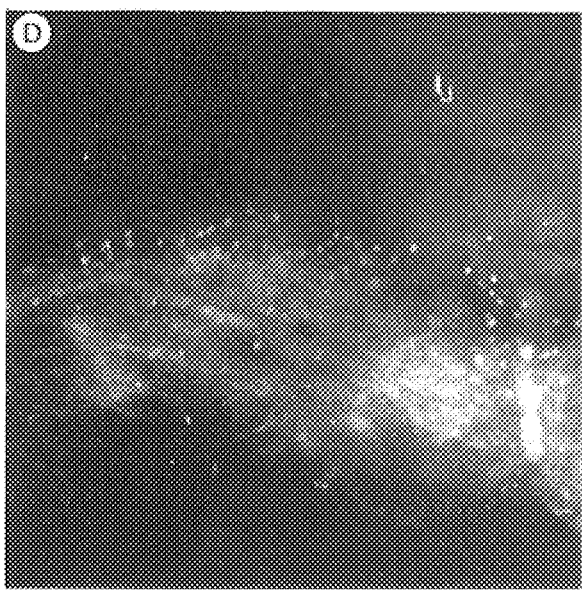

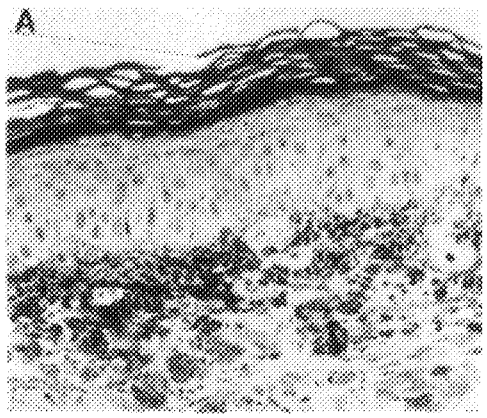
FIG. 2D-A
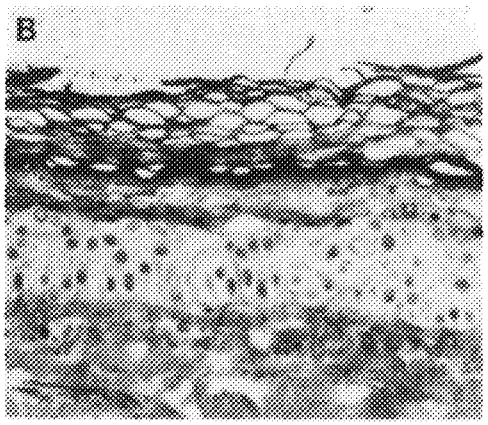
FIG. 2D-B
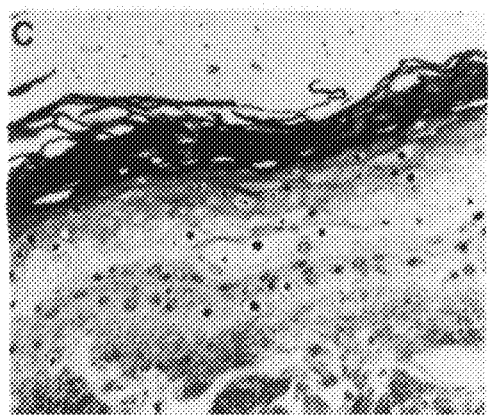
FIG. 2D-C

FIG. 7A-A
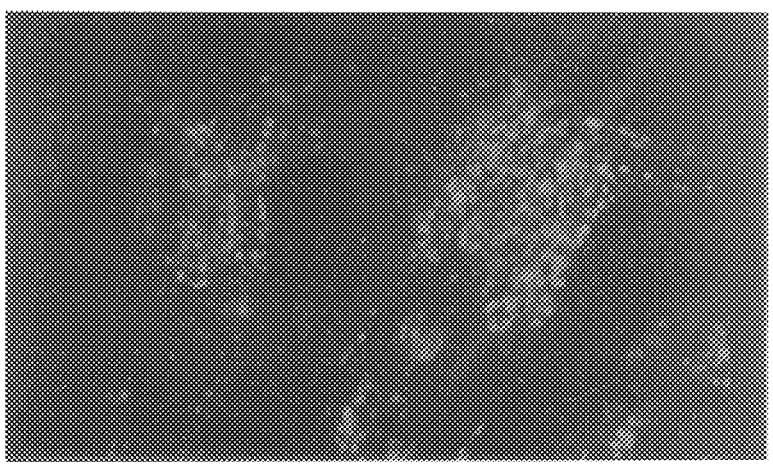
FIG. 7A-B
FIG. 7A-C

IN VITRO MICRO-ORGANS

CROSS REFERENCE

This application is a continuation-in-part of application Ser. No. 08/153,766 filed Nov. 17, 1993, now abandoned, and application Ser. No. 07/967,262 filed Oct. 27, 1992, now U.S. Pat. No. 5,387,576, both of which are herein incorporated by reference.

TECHNICAL FIELD

The present invention relates to growing microorgan cultures having a surface area to volume index of at least approximately 1.5 mm$^{-1}$ and being capable of cell proliferation and homeostasis for extended periods of time.

BACKGROUND OF THE INVENTION

Eukaryotic cell culture was first achieved in the early 1950s. Since that time, a wide range of transformed and primary cells have been cultivated using a wide variety of media and defined supplements such as growth factors and hormones as well as undefined supplements such as sera and other body extracts. For example, fibroblasts taken from a part of an animal such as the skin, can be routinely cultivated through many cell generations as karyotypically diploid cells or indefinitely as established cell lines. Epithelial cells however have morphological and proliferative properties that differ from fibroblasts are more difficult to cultivate. Indeed, in vitro, epithelial cells are commonly overgrown by fibroblasts when the two cells are grown together.

A diverse range of media have been developed for growing epithelial cells in a clonally competent manner. In some cases these cells can produce at least partially differentiated epithelium. Approaches to cultivation of epithelial cells in particular skin epithelia (keratinocytes) have included the following: cultivating cells on a feeder layer of lethally irradiated fibroblasts (Rheinhardt et al. 1975, *Cell* 6:331–343); cultivating keratinocytes on semi-synthetic collagen matrices (Eisenberg 1994, U.S. Pat. No. 5, 282,859; Bell 1990, EP 0361957); adding biological extracts including pituitary extracts and sera to specialized media; and utilizing a range of growth supplements including epidermal growth factor, and insulin (Boisseau et al. 1992, *J. Dermatol. Sci.* 3(2):111–120; Willie 1994, U.S. Pat. No. 5,292,655).
The skin.

Numerous attempts have been described for growing epithelial cells in such a way as to mimic human skin for purposes of wound treatment, in particular treatment of burns. The skin consists of two types of tissue. These are: (1) the stroma or dermis which includes fibroblasts that are loosely dispersed within a high density collagen matrix as well as nerves, blood vessels and fat cells; (2)the epidermis which includes an epidermal basal layer of tightly packed, actively proliferating immature epithelial cells. As the cells of the basal layer replicate, some of the young cells remain in the basal layer while others migrate outward, increase in size and eventually develop an envelop resistant to detergents and reducing agents. In humans, a cell born in the basal layer takes about 2 weeks to reach the edge or outer layer after which time the cells die and are shed. The skin contains various structures including hair follicles, sebaceous glands and sweat glands. Hair follicles are formed from differentiating keratinocytes that densely line invaginations of the epidermis. The open ended vesicles that formed from such invaginations collect and concentrate the secreted keratin and a hair filament results. Alternatively, epidermal cells lining an invagination may secrete fluids (sweat gland) or sebum (sebaceous gland). The regulation of formation and proliferation of these structures is unknown.

The constant renewal of healthy skin is accomplished by a balanced process in which new cells are being produced and aged cells die. There is a need to understand how this precise regulation comes about in order to counteract abnormal events occurring in aging, and also through disease and trauma that disrupt the balance. For example, psoriatic cells proliferate and die at an accelerated pace taking only about 15% of the time normally observed. Epidermal neoplasia arises when the epidermal cells multiply without control and rapidly overtake the number of cells normally dying. In chronic wounds, normal epidermal and dermal regeneration fails to occur.
Cultivation of skin in vitro.

Numerous attempts at growing skin in vitro have been undertaken. These attempts almost all include the step of separating the keratinocytes in the epidermis from fibroblasts and fat cells in the dermis. Where separation of keratinocytes is not performed, whole organs have been used. Attempts to cultivate organs in vitro have been limited to incubating organs in a serum containing medium (Li et al. 1991, *Proc. Natl. Acad. Sci.* 88(5):108–112). Where isolation of keratinocytes is performed, these cells are grown in a manner that permits the formation of a stratified epidermis. The epidermis prepared in this manner lacks hair follicles and sweat glands and the natural relationship between the epidermis and the dermis is not preserved. Cultivation methods including growing keratinocytes on non viable fibroblasts (Rheinwald et al. 1975, *Cell* 6:331–343); or placing the keratinocytes from the animal on a dermal substrate of collagen and fibroblasts that is synthetic or has been derived from an alternative source from that of the epidermis (Sugihara et al. 1991, in vitro Cell Dev. Biol. 27:142–146; Parenteau et al. 1991, *J. Cell Biochem.* 45(3): 245–251).

Most existing in vitro models of the epidermis lack hair follicles, sweat glands and sebaceous glands (for a review of epidermal cell culture, see Coulomb et al. 1992, *Pathol. Biol. Paris,* 40(2):139–146). Exceptions include the gel-supported skin model of Li et al. (1991) who utilized skin explants with dimensions of 2×5 mm$^2$ and 2.0 mm thick that remained viable for several days in the presence of serum containing media.

It would be desirable to have an in vitro model of the skin in a serum free environment where the natural intercellular relationships that occur in vivo are maintained so as to more accurately study how skin is formed and remains viable. For example, insights into how hair follicle formation occurs would have significant therapeutic applications including treatment for balding men, for patients undergoing chemotherapy and for skin grafting.

An in vitro model of the skin that closely mimics the properties of skin in vivo would have utility in screening assays in which compounds could be tested for their ability to repair or damage the skin (Kao et al. 1985, *Toxicol. Appl. Pharmacol.* 81:502–516; Goldberg ed. 1989, *Alternative Methods in Toxicology,* vol. 7, pp. v–vi, New York:Liebert). Requirements of a reproducible model for screening might include consistency in tissue architecture and nutritional environment in vitro, as well as prolonged viability and proliferation of cultures beyond 24 hours to observe threshold effects of compounds being screened. This level of consistency cannot be achieved in the presence of undefined media supplements such as sera or tissue extracts that vary between batches and cannot be adequately controlled. The dependence of a model on external growth supplements such as growth factors is also undesirable as growth factors or hormones may be included among the compounds to be tested. At present, existing in vitro skin models either require exogenous factors (Boyce et al. 1983, *J. Invest. Dermatol.* 81:33–4) or serum (Li et al. 1991, *Proc. Natl. Acad. Sci.* 88(5):108–112) or are only viable for short periods of time. Epithelia.

The skin is one example of an epithelial tissue supported by stromal tissue containing fibroblasts. Epithelial tissues are found in every part of the body where an interface between an organ and the environment arise. Epithelial cells cycle continuously in an uninjured body and form the covering tissue for all the free surfaces in the body including the skin. In some cases, such as in the pancreas, the epithelial cells line numerous invaginations and secrete enzymes into open spaces that enable the organ to function. The lung is another example of a highly invaginated organ, each invagination in the lung being lined with epithelial cells through which air diffuses from the environment in to the body. Once again, these epithelial ells have characteristic properties. The lining of the gut is also composed of specialized epithelial cells that not only form a barrier but contain specialized structures for selectively absorbing food. All the epithelia are supported by a stroma of connective tissue.

There is a need for in vitro methods of culturing and maintaining organ cultures in which the cells preserve their naturally occurring intracellular relationships for extended periods of time. The availability of a tissue model in which differentiation, cell proliferation and cell homeostasis occurs would have utility in understanding the mechanisms by which organs are maintained in a healthy state and consequently how abnormal events may be reversed.

SUMMARY OF THE INVENTION

This invention satisfies the above needs. A novel in vitro micro-organ culture is provided that in a preferred embodiment comprises a population of animal cells outside of an animal, corresponding to cells inherent in an organ, the cells being grouped so as to preserve the natural affinity of one cell to another, the dimensions of the cell grouping having a surface area to volume index of at least approximately 1.5 $mm^{-1}$, and being capable of at least one of cell proliferation and cellular homeostasis, the population of animal cells being maintainable in a nutrient medium for a period of time in excess of 24 hours.

A further embodiment of the invention includes a method for forming an in vitro microorgan culture, comprising obtaining a population of animal cells outside of an animal, corresponding to cells inherent in an organ, the cells being grouped so as to preserve the natural affinity of one cell to another, the dimensions of the cell grouping having a surface area to volume index of at least approximately 1.5 $mm^{-1}$, being capable of at least one of cell proliferation and cellular homeostasis and placing the cells in nutrient medium for a period of time in excess of 24 hours.

A further embodiment of the invention includes a method of screening a compound for biological activity which comprises forming an in vitro microorgan culture as described above, exposing the culture to the compound and measuring a change in any of cell proliferation, cellular homeostasis or cell differentiation in the presence of the compound.

A further embodiment of the invention includes a method of repairing a non-healing wound in an animal subject, having the following steps including selecting a population of cells from an animal subject; sectioning the population of cells into a plurality of segments so that the surface area to volume index is at least approximately 1.5 $mm^{-1}$; and applying the population of cells of step (b) so as to replace or supplement the endogenous tissue.

A further embodiment of the invention includes a method directed to modifying cell proliferation in a mammalian tissue, comprising; identifying a compound capable of modifying normal proliferation and homeostasis of a microorgan culture as described above, and administering the compound to an animal subject.

BRIEF DESCRIPTION OF THE DRAWINGS

These and other features, aspects and advantages of the present invention will become better understood with reference to the following description, appended claims and accompanying drawing where

FIG. 2c is a micrograph showing immunofluorescence corresponding to replicating cells of mouse x50 (a), guinea pig x75 (b) human foreskin x50 (c) and human foreskin x 75 (d).

FIG. 2d. Transverse section of human micro-organ explants. (mag x75) showing tissue architecture at zero (a), three(b) and six(d) days in culture.

FIG. 6 is a histogram showing $^3$H-Thymidine incorporation in proliferating cells in microorgan cultures of the colon, liver, kidney, duodenum and esophagus, at 3 days, 4 days and 6 days of "in vitro" cultivation.

FIG. 7a is a micrograph showing active proliferation of hair follicles in micro-organ cultures as determined by immunofluorescence. Magnification (a) x 40,(b) and (c)x 75.

DETAILED DESCRIPTION OF SPECIFIC EMBODIMENTS

The present invention is directed to an in vitro model system in which epithelial cells undergo at least one of cell proliferation and cellular homeostasis according to that found in nature. Cellular homeostasis is defined here and in the claims as an equilibrium between cell proliferation and cell loss in which the tissue as a whole remains viable but may not necessarily grow despite continued growth of individual cells within the tissue. In this context, cell loss may arise for example from cell death or cell sloughing. For example, gut derived epithelia contain a very active proliferative population of cells that divide every 24 hours while maintaining a constant size.

A population of cells is defined here and in the claims as a number of cells of one or more types that may coexist together.

Figure 1:
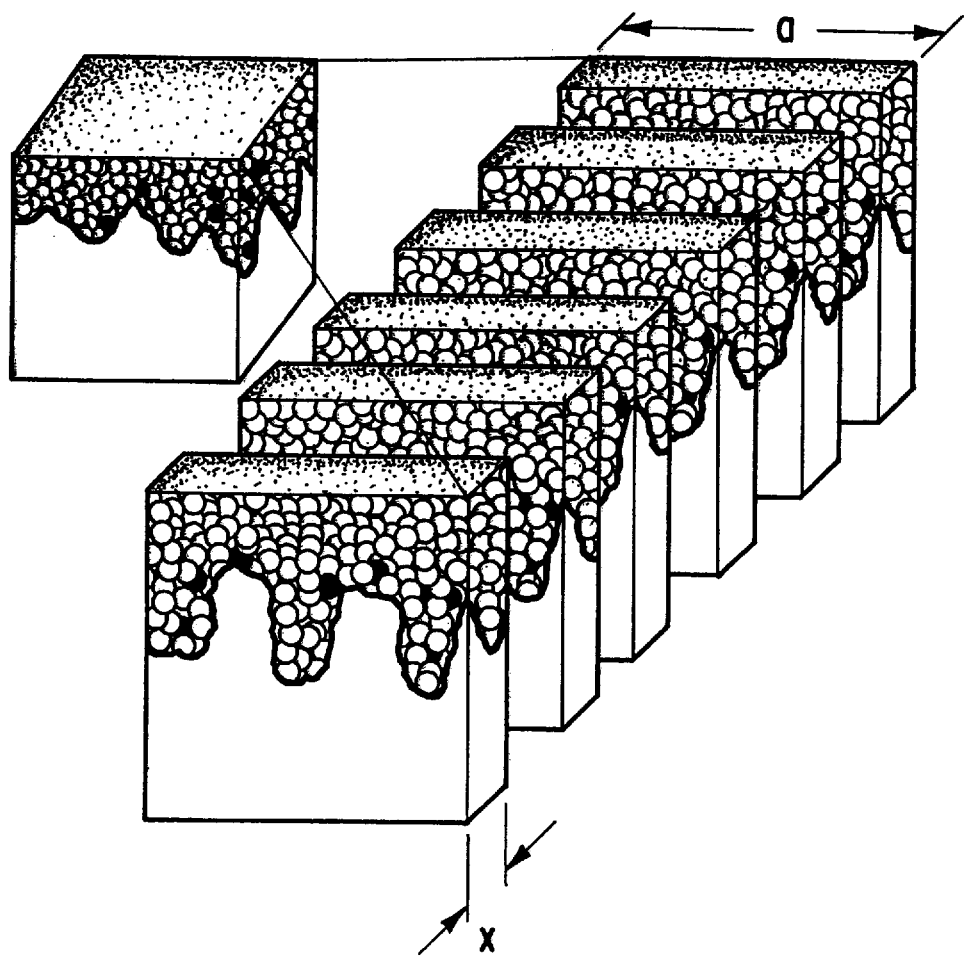
FIG. 1 is a diagrammatic representation of a micro-organ depicting the dimensions that determine Aleph where x=thickness and a=width of the tissue.

The surface area to volume index is defined here and in the claims as Aleph where: Aleph $=1/x+1/a>1.5$ mm$^{-1}$ and x=tissue thickness and a=width of tissue in millimeters as shown in FIG. 1.

The third dimension has been ignored in determining the surface area to volume index because variation in the third dimension causes ratiometric in both volume and surface area. However, when determining Aleph, a and x should be defined as the two smallest dimensions of the tissue slice.

The surface area to volume index.

A unique aspect of the invention is the similar availability of nutrients to all cells in the tissue by diffusion. The availability of nutrients to cells in a three dimensional structure is similar to that of cells in a monolayer according to the invention. The diffusion of nutrients to every cell in a three dimensional organ culture requires a minimum level of accessibility to each cell absent specialized delivery structures or synthetic substrates. This accessibility can be maintained if Aleph is at least approximately 1.5 mm$^{-1}$ where Aleph is an index calculated from the thickness and the width of the tissue.

Examples of Aleph are provided in Table 1 where for example, a tissue having a thickness (x) of 0.1 mm and a width (a) of 1 mm would have an Aleph index of 11. In example 1, the tissue has x=0.3 mm and a=4 mm so that Aleph=3.58. In Example 3, x is varied and a is constant at 4 mm. It can be seen from FIG. 3, that proliferative activity is substantially reduced as the thickness of the explant increases. Accordingly, at 900 μm thickness, the number of proliferating cells in a microorgan culture is about 10 fold less then in tissue from a similar source having a thickness of 300 μm. The Aleph index for a tissue having a thickness of 900 μm is 1.36, below the minimum described here and in the claims whereas the aleph index for tissue having a thickness of 300 μm is 3.58mm$^{-1}$ which is well within the range defined here and in the claims.

TABLE 1

Different values for the surface area to volume ratio index "Aleph", as a function of a (width) and x (thickness) in mm$^1$

| a(mm)/ x(mm) | 1 | 2 | 3 | 4 | 5 |
|---|---|---|---|---|---|
| 0.1 | 11 | 10.5 | 10.33 | 10.25 | 10.2 |
| 0.2 | 6 | 5.5 | 5.33 | 5.25 | 5.2 |
| 0.3 | 4.3 | 3.83 | 3.67 | 3.58 | 3.53 |
| 0.4 | 3.5 | 3 | 2.83 | 2.75 | 2.7 |

TABLE 1-continued

Different values for the surface area to volume ratio index "Aleph", as a function of a (width) and x (thickness) in mm$^1$

| a(mm)/ x(mm) | 1 | 2 | 3 | 4 | 5 |
|---|---|---|---|---|---|
| 0.5 | 3 | 2.5 | 2.33 | 2.25 | 2.2 |
| 0.6 | 2.66 | 2.16 | 2 | 1.91 | 1.87 |
| 0.7 | 2.4 | 1.92 | 1.76 | 1.68 | 1.63 |
| 0.8 | 2.25 | 1.75 | 1.58 | 1.5 | 1.45 |
| 0.9 | 2.11 | 1.61 | 1.44 | 1.36 | 1.31 |
| 1 | 2 | 1.5 | 1.33 | 1.25 | 1.2 |
| 1.2 | 1.83 | 1.3 | 1.16 | 1.08 | 1.03 |
| 1.3 | 1.77 | 1.26 | 1.1 | 1.02 | 0.96 |
| 1.6 | 1.625 | 1.13 | 0.96 | 0.88 | 0.83 |
| 2 | 1.5 | 1 | 0.83 | 0.75 | 0.7 |

Source of microorgans capable of homeostasis and proliferation in vitro.

In an embodiment of the invention, populations of cells are grouped in a manner that preserves the natural affinity of one cell to another. For example, in skin micro-organ cultures, keratinocytes of the epidermis remain associated with the stroma and the normal tissue architecture is preserved including the hair follicles. Such an association facilitates intercellular communication. Many types of communication takes place among animal cells. This is particularly important in differentiating cells where induction is defined as the interaction between one (inducing) and another (responding) tissue or cell, as a result of which the responding cells undergo a change in the direction of differentiation. Moreover, inductive interactions occur in embryonic and adult cells and can act to establish and maintain morphogenetic patterns as well as induce differentiation (Gurdon (1992) Cell 68: 185–199).

The micro-organ cultures prepared according to the invention as described in Example 1, comprise a population of cells grouped in a manner that may include a plurality of layers so as to preserve the natural affinity of one cell to another. The proliferation of individual cells or groups of cells can be observed and followed by autoradiography or immunofluorescence.(Example 2, FIG. 2).

Micro-organ cultures from animals including adult human skin, mouse, guinea pig and rat skin have been isolated and grown for up to 21 days in culture. However, it is within the scope of the invention to maintain cultures for extended periods of time beyond 21 days.

Furthermore, it is within the scope of the invention to form micro-organ cultures from a wide range of animals. The range of animals are merely exemplified but is not limited to the sample provided in Example 2.

Micro-organ cultures were prepared from skin (Examples 1 2,3, 7 and 8) and also from organs including the mammalian pancreas, liver, kidney, duodenum, esophagus and bladder (Example 4, 5 and 6). Similarly, microorgan cultures of epithelia from mammalian cornea, kidney, breast tissue and various gut derived tissues in addition to the esophagus such as intestine and colon may also be prepared using the methods of the invention. Indeed, it is within the scope of the invention to isolate and maintain microorgan cultures from any site which contains an epithelial stromal architecture within the body.

The growth medium.

There are a large number of tissue culture media that exist for culturing cells from animals. Some of these are complex and some are simple. While it is expected that microorgan cultures may grow in complex media, it has been shown here that the cultures can be maintained in a simple medium such as Dulbecco's Minimal Essential Media. Furthermore, although the cultures may be grown in a media containing sera or other biological extracts such as pituitary extract, it has been shown here that neither sera nor any other biological extract is required. Moreover, the organ cultures can be maintained in the absence of sera for extended periods of time. In preferred embodiments of the invention, growth factors are not included in the media during maintenance of the cultures in vitro.

The microorgan cultures may be maintained in any suitable culture vessel such as a 24 or 96 well microplate and may be maintained at 37° C. in 5% CO2. The cultures may be shaken for improved aeration, the speed of shaking being for example 12 rpm.

Measuring the biological properties of micro-organ culture

The microorgan cultures of the present invention derived from normal tissue have been shown to maintain a state of homeostasis with proliferation of constituent cells without overall growth of the tissue.

Methods of measuring cell proliferation are well known in the art and most commonly include determining DNA synthesis characteristic of cell replication. There are numerous methods in the art for measuring DNA synthesis, any of which may be used according to the invention. In an embodiment of the invention, DNA synthesis has been determined using a radioactive label ($^3$H-thymidine) or labelled nucleotide analogues (brdU) for detection by immunofluorescence.

Micro-organ cultures can be formed and maintained not only by the proliferation of mature cells but also by the active participation of precursor cells including in some instances, embryonic cells. The micro-organ cultures have been shown to represent a suitable environment for preserving and facilitating the natural evolution of these precursor cells. For example, the immature cells of the basal layer have been observed to become mature keratinocytes in skin microorgan cultures. (FIG. 3(b)). Similarly, embryonic pancreatic cells can provide a mature pancreatic epithelium in microorgan cultures. The maturation of precursor cells and their subsequent functioning as adult cells can be monitored by measuring secretion of specialized products such as specific keratins in epidermal cells and insulin, Glut 2 and glucagon in pancreatic epithelia.

The micro-organ cultures prepared according to the invention preserve the normal tissue architecture that is present in vivo. This includes the maintenance of hair follicles, sweat glands and sebaceous glands in skin microrgans in vitro according to their normal occurrence in vivo (Examples 7 and 8 and FIGS. 7a, 7b and 8). Because these cultures can be maintained in controlled and uniform conditions and yet they closely resemble tissue in vivo, they provide a unique opportunity to observe, measure and control natural phenomena and the perturbation of natural phenomena arising from disease, aging or trauma. Furthermore, the ready availability of techniques to study individual cells at identified sites on the culture, provide insights into the functioning of individual components of the tissue as they interact with each other as well as the whole tissue.

Applications of microorgan cultures

Applications of the microorgan cultures include the following:

(a) identification of factors involved in normal homeostasis of tissues and cells;

(b) the effect on the normal homeostasis of tissues and cells of changes in the environment of the cells including changes in nutrients and the presence of potentially toxic agents;

(c) the pathway of changes in the tissues and cells that are triggered at the beginning and during pathogenesis or trauma;

(d) identification of repair mechanism that reverse the adverse effects in an altered environment associated with pathogenesis or trauma;

(e) developmental regulation of cells that differentiate during the normal homeostasis of the tissue;

(f) developmental regulation of specialized structures within the tissue such as hair follicles; and (g) organ supplementation where pieces of an individual's organ remains but are insufficient for replacing or regenerating damaged tissue such as occurs in patients with chronic skin ulcers which have healing deficiencies caused by inappropriate blood supply, or where the local skin is unable to heal such as in the condition known as type 1 or type 11 diabetes.

Regulation of wound healing

Repair of skin lesions is known to be a highly complex process that includes primary epithelial cell migration as well as replication of epidermal cells in response to molecular signals from underlying connective tissue. Skin microorgan cultures have been used here as a model for wound healing. Under controlled culture conditions, factors controlling healing can be carefully monitored. Furthermore, since the culture is isolated from the natural blood supply, analysis of the healing process can be done without the additional complexity of blood borne factors or cells. Normal epidermis has a low mitotic activity with cells cycling every 200–300 hours. When the epidermis is wounded, a burst of mitotic activity takes place so that the cells divide up to 10 times faster depending on the conditions and severity of the wound (Pinkus H., J.Invest. Dermatol. 16: 383–386 (1951)). In Example 2, we have shown that the microorgan cultures show increased proliferation of up to 10 fold for several days. In this example, the edge of a wound is comparable to the microorgan culture. This increased proliferation mimics the events that are associated with wounding and provide a unique opportunity to study the process of wound healing. We have demonstrated in vivo that microoexplants can be applied to chronic wounds (Example 9) and can form a viable implant capable of growing hair (Example 10).

Regulation of tumor formation and growth

A preferred embodiment of the invention is directed to inhibition of epithelial tumor formation and growth. Tumor formation arises as a consequence of alterations in the control of cell proliferation and disorders in the interactions between cells and their surroundings. The patterns of growth of a variety of rapidly growing, transplantable and malignant tumors of epithelial origin are organized tissues with characteristic histological patterns. The establishment of the basic pattern depends first on the connective tissue adjacent position of the mitotic cells, a medial sheath of differentiated aging cells and an inner mass of dying cells. Except that the tumor forms a cyst instead of a sheet, the cells are stratified in a manner that is similar to the epidermis. In this situation, cell production exceeds cell loss.

Data is presented here (Example 9, FIG. 9) in which microorgan cultures of the skin have been used for screening compounds for biological activity. In this example, TGF-β was tested and found to act as an inhibitor of cell proliferation. This model more accurately reproduces the structure of in vivo skin than any previous model. Activin has also been shown to inhibit proliferation of epithelial cells. This protein is a member of the TGF-β superfamily and as such suggests that there may be other members of this family that play a role in inhibition of proliferation of epithelial cells. The data suggests a role for proteins in the TGF-β family as significant regulators of epidermal homeostasis and in inhibiting epithelial tumor formation and growth in vivo.

EXAMPLE 1

Preparation of Microorgan Cultures of Epidermis

Fresh skin was obtained after surgery, cleaned from underlying fat tissue and cut into 0.4×5 cm flaps, which are then transversely sectioned, using a tissue chopper or other suitable cutting means into 300 μm sections under sterile conditions so that the final tissue segments had dimensions of 4 mm in width and 0.3 mm in thickness (see FIG. 1). These microorgans were placed in a 24-well microplate in 400 μl of DMEM in the absence of serum under 5% $CO_2$ at 37° C., under constant shaking at 12x rpm for periods of 1 to 8 days. Twenty micro-explants were grown per well.

EXAMPLE 2

Measurement of the Proliferation of Cells in Vitro in Epidermis Culture Derived from Mice, Guinea Pigs and Humans Microorgan cultures were prepared according to Example 1 and proliferation of cells was measured by analyzing the amount of DNA synthesis as follows:

Mouse skin and guinea pig skin were grown for 2 days and human foreskin was grown for 4 days after which brdU was added to the medium in a final concentration of 100 μM for 3 hrs, followed by fixation of the cells in 4% formaldehyde. After fixation, the cultures were stained with goat anti-brdU antibodies followed by anti-goat-FITC labeled IgG. Histological preparations were embedded in epon after fixation in 4% formaldehyde and cut into 3 μm slices and stained with methylene blue.

Figure 2A:
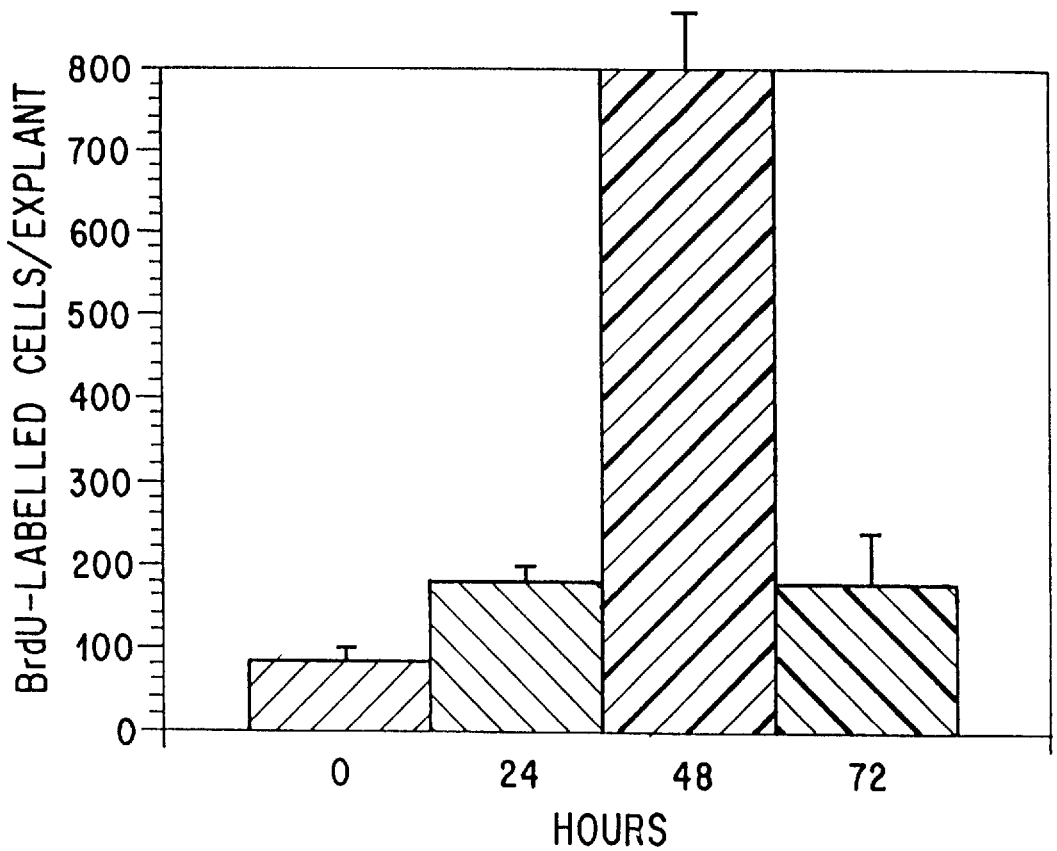
FIG. 2a is a histogram showing cell proliferation in a guinea pig micro-organ culture as determined by BrdU labelling after incubation for different time periods.
Figure 2B:
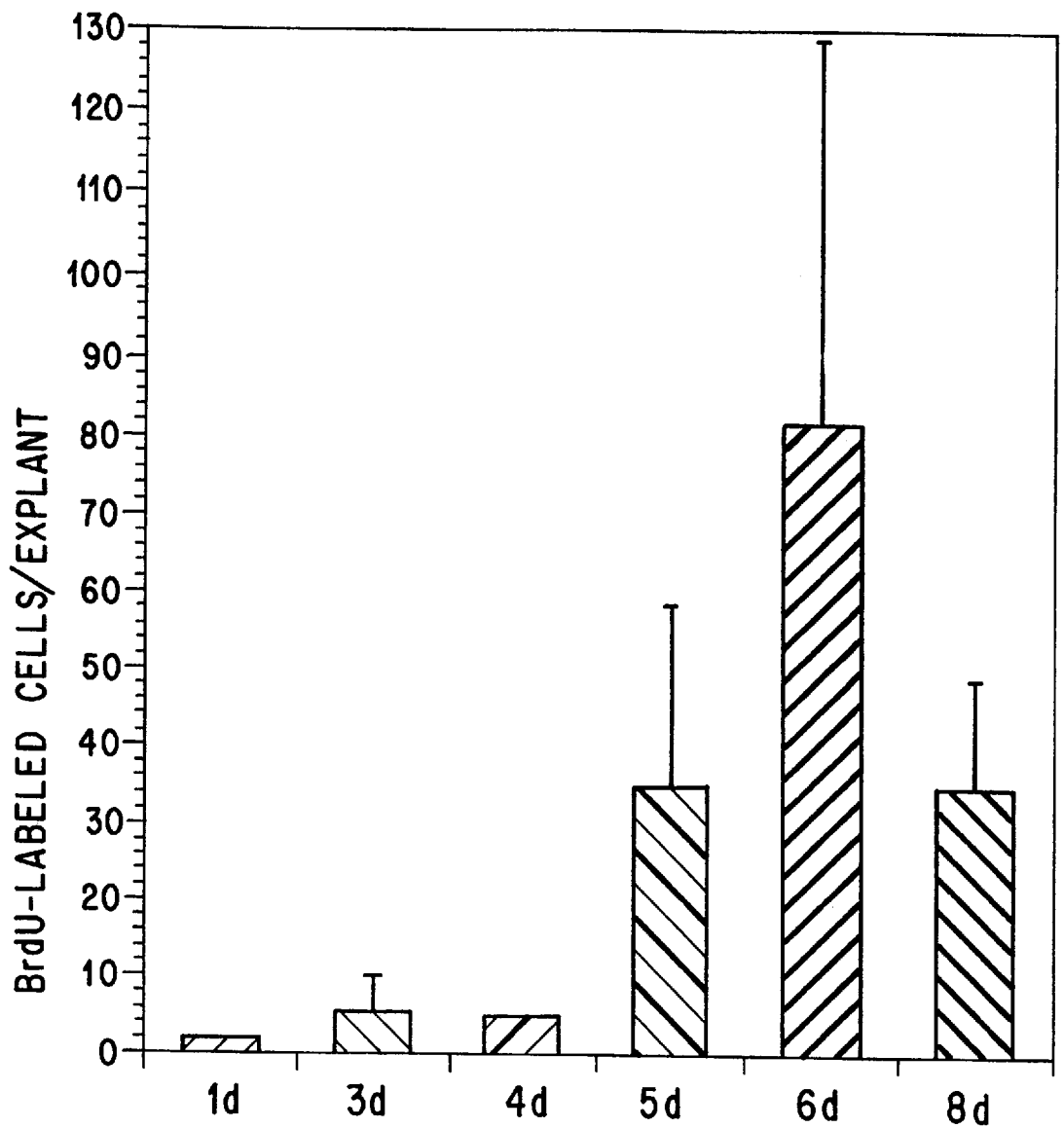
FIG. 2b is a histogram showing cell proliferation in a human back skin micro-organ culture as determined by BrdU labelling after incubation of cultures for 1–8 days.

It was found that the fraction of cells synthesizing DNA in vitro after 2 to 4 days in culture increased up to 10 fold compared with the values observed in vivo, after which the rate of DNA synthesis gradually decreased but remained high for up to 10 days in culture (see FIGS. 2a. b. c). Even at six days in culture, the cells maintained a steady state of proliferation and differentiation so that the tissue architecture was preserved (FIG. 2d).

EXAMPLE 3

Measurement of the Proliferation of Cells within a Microorgan of Various Sizes

Figure 3:
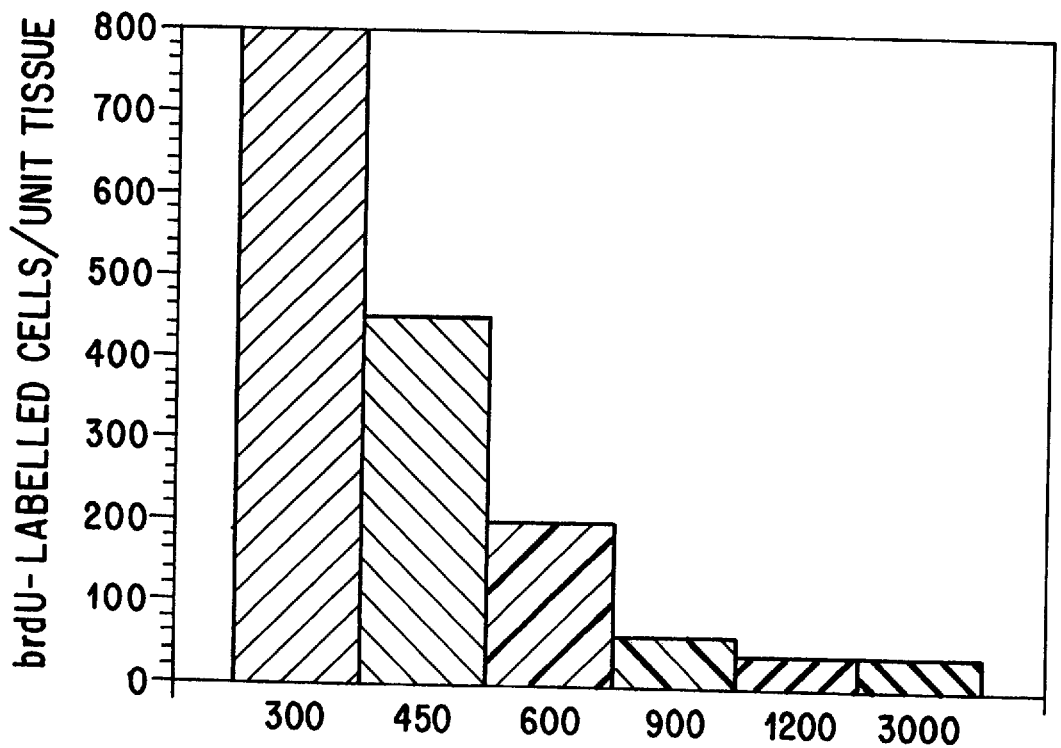
FIG. 3 is a histogram demonstrating the effect on epidermal proliferation of varying thickness (x) of guinea pig skin microorgan cultures using BrdU incorporation where (a) has been kept constant at 4 mm.

Guinea pig micro organs were prepared as in Example 1. Whole thickness skin strips 4 mm in width were sectioned into explants of varying thicknesses including slices of 300, 450, 600, 700, 900, 1200 and 3000 μm thickness. These slices were placed individually into wells containing serum free medium for 2 days. BrdU was added for 4 hrs before termination at a final concentration of 100 μM. The explants were then fixed in 4% formaldehyde and stained with goat antibodies to BrdU followed with a anti-goat IgG FITC labelled antibody preparation. The results are shown in FIG. 3. The amount of brdU incorporation as a factor of the number of cells/unit tissue is significantly reduced as the thickness of the explants increase.

EXAMPLE 4

Figure 4A:
FIG. 4 is a micrograph showing immunofluorescence corresponding to proliferating cells in pancreas derived microorgan cultures (mag x75).
Figure 4B:
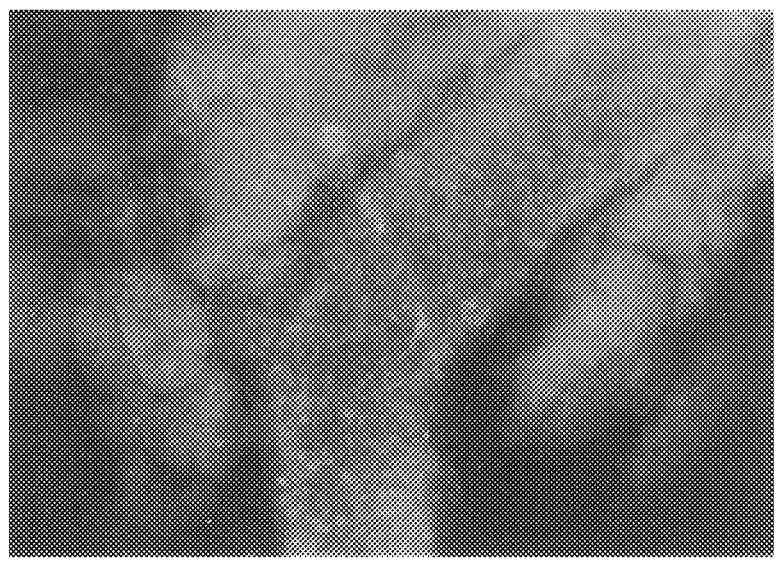

Preparation of Microorgan Cultures from the Pancreas and Measurement of Cell Proliferation within the Culture Guinea-pig pancreas was removed and then cut into sections of 300 μm in thickness, 4 mm in width and 2 mm in depth. The micro-explants were grown in culture for several time periods from 2 to 18 days. Seven micro-organs were placed in each of 96 wells of a plate in 150 μl DMEM in the absence of serum under 5% $CO_2$ at 37° C. under constant shaking at 12 RPM. BrdU was added 3 hrs before termination at a final concentration of 100 μM and the explants were then fixed in 4% formaldehyde and stained with goat antibodies to BrdU followed by anti-goat-FITC labeled IgG. FIG. 4 illustrates that cells in the pancreas derived microorgans are actively proliferating.

EXAMPLE 5

Figure 5:
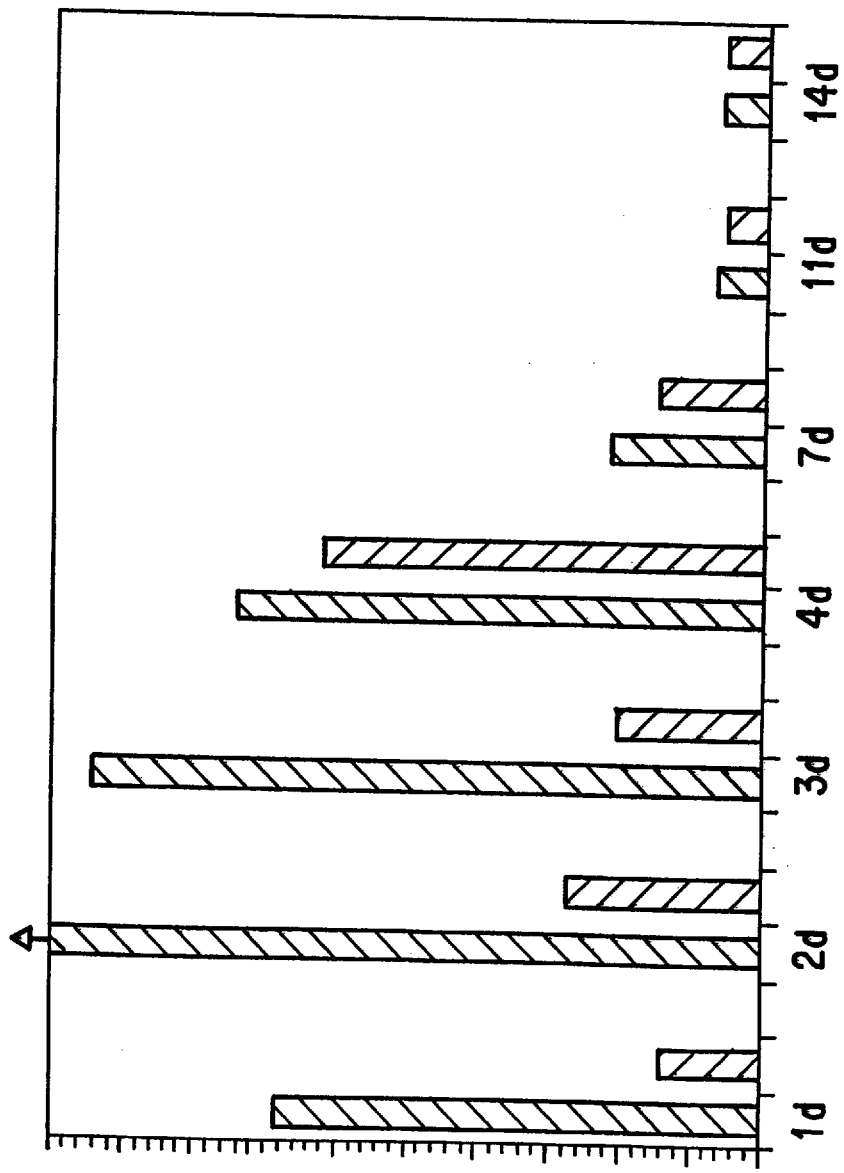
FIG. 5 is a histogram showing amounts of insulin released by adult pig pancreas microorgan cultures.

Preparation of Microorgan Cultures from the Pancreas and Measurement of Insulin Secretion into the Medium Adult pig pancreas microorgan cultures were prepared as in the previous examples for skin. Pancreases were removed, cut with scissors to an approximate depth of 2 mm and sliced into sections 300 μm thick having a width of 4 mm. The microcultures were grown for 14 days in serum free medium. Every two days, the medium was removed and fresh medium added. Collected media was assayed for insulin content using standard radioimmunoassay methods. (FIG. 5)

EXAMPLE 6

Figure 6:
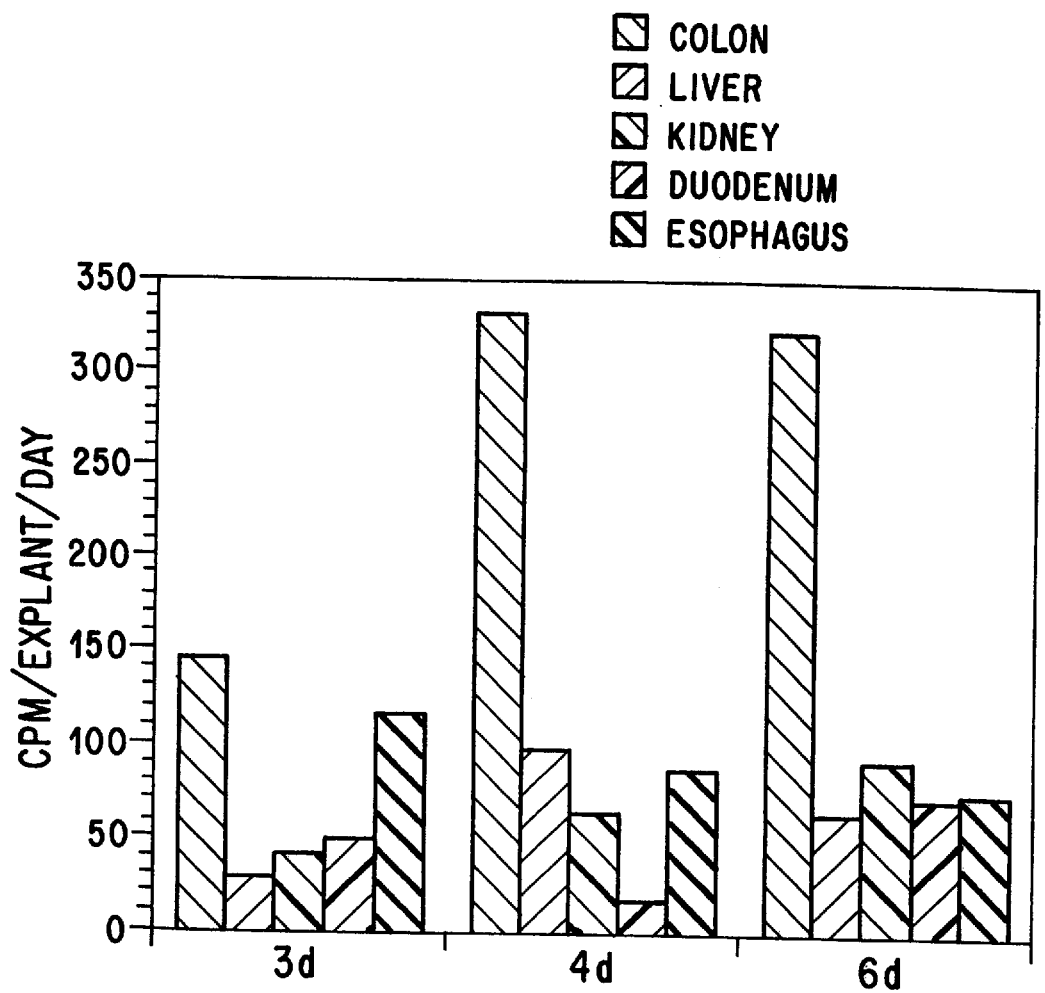
FIG. 6 is a histogram showing $^3$H-Thymidine incorporation in proliferating cells in microorgan cultures

Preparation of Microorgan Cultures from the Liver, Kidney, Duodenum, Esophagus and Bladder and Measurement of Cell Proliferation within the Culture Guinea-pig microorgan micro-cultures from several epithelial containing organs were prepared as in previous examples for skin. Organs were removed and with scissors, were cut to an appropriate width of 2 mm and sliced into sections of 300 μm thick. The microcultures were incubated for 3,4,and 6 days in serum free medium. 12 hours before termination of the experiment, $^3$H-thymidine was added to the cultures of explants. At termination, the tissue was fixed, rinsed several times and counted in a scintillation counter. The results are shown in FIG. 6 where all tissues exhibit active proliferation which continues through 6 days as determined by uptake of $^3$H-thymidine.

EXAMPLE 7

Proliferation of Hair Follicles in vitro.

Figure 7B:
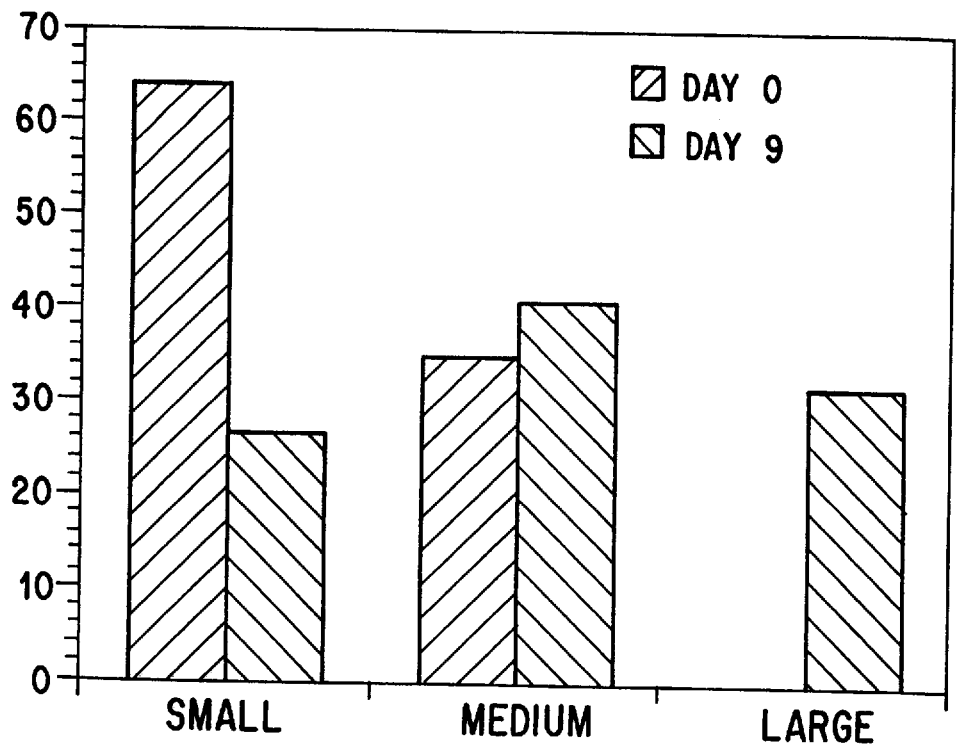
FIG. 7b is a histogram showing the size distribution of hair shafts at the beginning and end of the microculture.

Epidermis was prepared according to Example 1 and incubated for 2 days. BrdU was added 3 hrs before termination of incubation. Cells were fixed in 4% formaldehyde and stained with goat anti-brdU antibodies followed by anti-goat-FITC labelled IgG. Intact hair follicles that were present in vivo in their normal surroundings could be maintained under precisely controlled culture conditions, without the need of add serum or any other exogenous factor. Hair follicle cells in these microorgans were found to proliferate vigorously for several days under the conditions of the present method as indicated by the large number of hair follicles cells that incorporated brdU (FIG. 7a). The size distribution of hair shafts at time zero of a micro-organ guinea pig culture and after 2 weeks is shown in FIG. 7b. The medium was exchanged every two days. Hair shaft size have been arbitrarily classified as small, medium and large. After 9 days in culture, there is a clear shift in size distribution so that the percentage of small hairs decreased from 64% to 28%, while large shafts which were not present at the beginning of the culture now represented 30% of the shaft population.

EXAMPLE 8

Preparation of a Screening Assay for Measuring the Effect of an External Agent on Cell Proliferation The cultures were prepared and maintained in defined medium in similar growth conditions as described in Example 1. Control samples were analyzed by immunocytochemistry to determine that the microorgan culture was maintained in a manner that was similar to that occurring in vivo.

Figure 8:
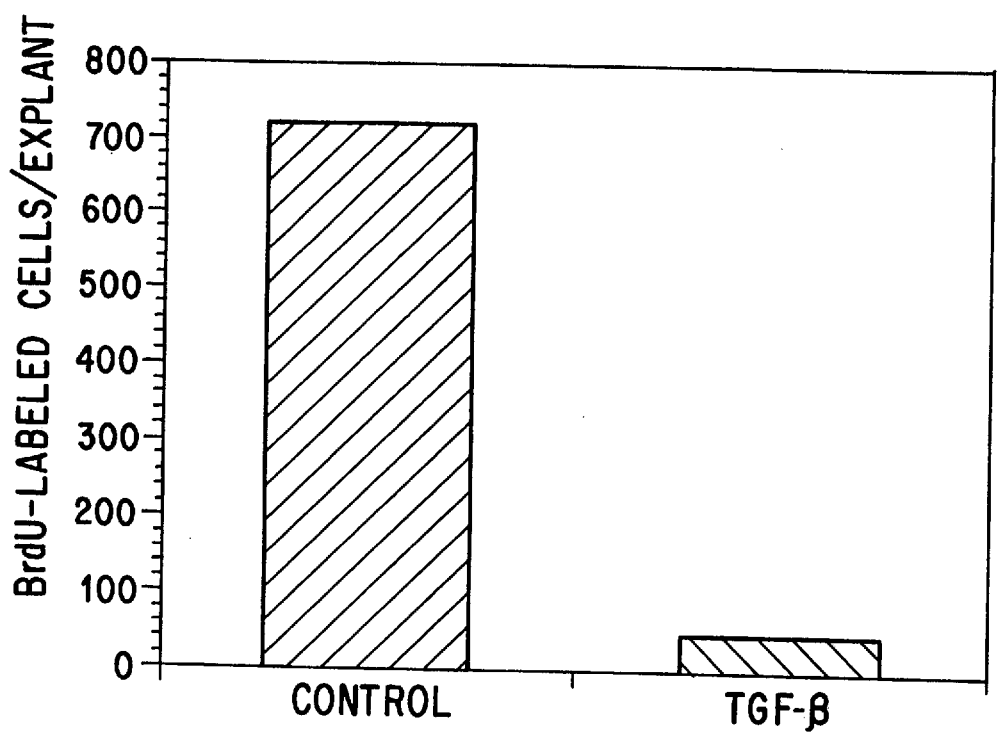
FIG. 8 is a histogram showing the inhibition of mitogenesis in microorgan cultures in the presence of 2.5 ng/ml TGF-β in guinea-pig skin cultures

Duplicated samples of skin micro-cultures were treated with TGF-β at 2.5 ng/ml. A quantitative analysis of the number of BrdU labelled cells/explant was performed according to Example 2. Greater then 90% inhibition of DNA synthesis was observed in the presence of TGF-β compared with controls (FIG. 8).

EXAMPLE 9

A Method of Treating Patients with Chronic Non-Healing Skin Ulcers.

Figure 9:
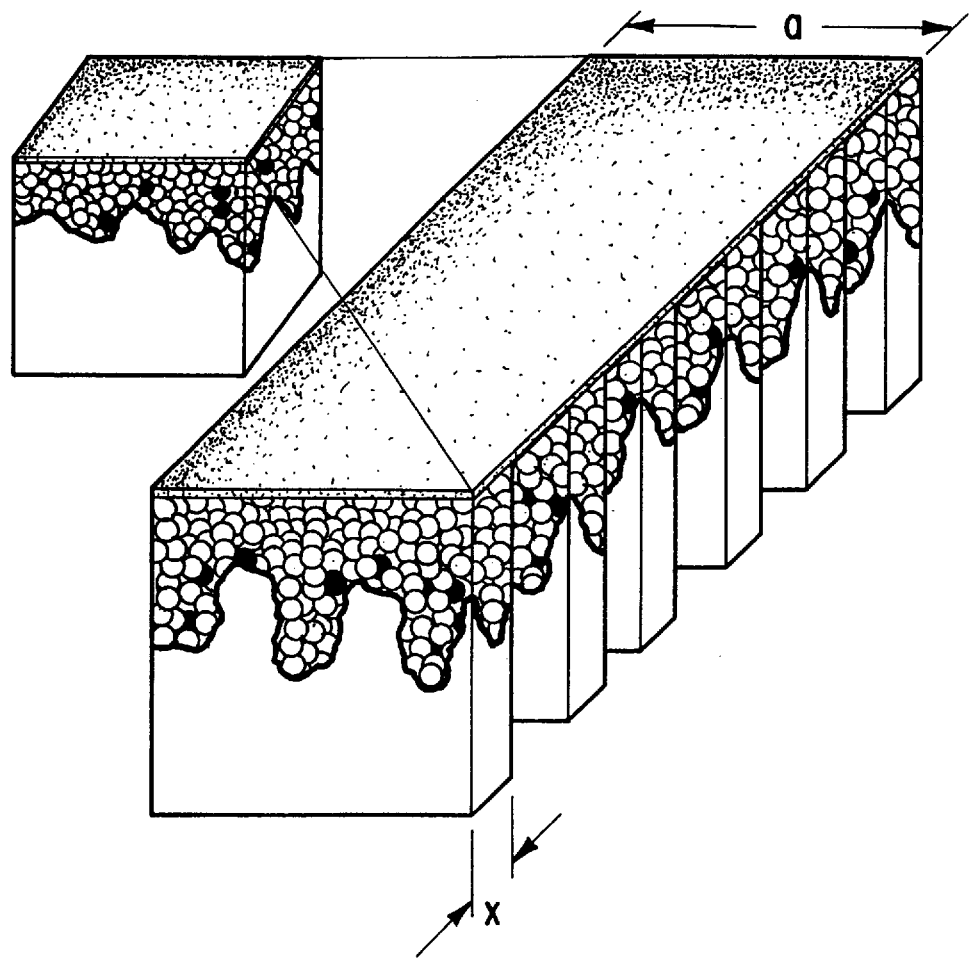
FIG. 9 is a diagrammatic representation of a microorgan explant for treatment of chronic skin ulcers showing incomplete sectioning of tissue slices so as to maintain a structure that can be readily manipulated in vivo.

According to this method, a small-area of normal, uninvolved skin autograph is removed from the patient and full-thickness microexplants of 4 mm in width and 0.3 mm thick is prepared as described in Example 1. The preparation however differs from Example 1 in that the sectioning into 0.3 mm slices is deliberately incomplete so that a series of sections are held together as indicated in FIG. 9, the upper epidermal layers including the stratum corneum. The design of this implant is directed to permitting the nutrients to reach all the cells but maintaining the tissue slices in a manipulatable format. The patient's wound is cleaned and surrounding skin edges are removed. The area devoid of skin is then carefully covered by the micro-explants, which are placed on the wound such that the non-sectioned edge is facing outermost and the opposing sectioned pieces are suspended in the fluid within the wound. Sufficient micro-explants are prepared to substantially cover the wounded area. The treated region is then covered with a suitable dressing and allowed to heal.

EXAMPLE 10

Proliferation of Hair Follicles in vivo

Figure 10:
FIG. 10 is a photograph of the surface of a mouse after removal of a piece of normal skin and subsequent replacement with a micro-organ culture showing healing and generation of new hair shafts in the implant that has become incorporated in the mouse host (mag x10).

An in vivo animal experiment was performed where a 1 cm$^2$ area of skin was removed from a mouse and incompletely microsectioned so that the stratum corneum of the whole skin area was left intact as described in Example 9. The microorgan was reimplanted into its original position in the mouse, stitched and allowed to heal. The implant remained viable, became incorporated into the animal tissue and new hair shafts grew from the implant after 1–2 weeks in culture. (see FIG. 10).

Although certain preferred embodiments of the present invention have been described, the spirit and scope of the invention is by no means restricted to what is described above.

I claim:

1. A micro-organ culture, comprising:
   (i) a nutrient medium in a culture vessel, the vessel having therein an oxygen concentration not substantially greater than that in the atmosphere; and
   (ii) a population of non-fetal animal cells disposed in the nutrient medium for greater than 24 hours, wherein the population is derived form an organ, the organ having an in vivo tissue structure including an epithelial tissue and an adjacent stroma, wherein the epithelial tissue has a first surface corresponding to an exterior surface of the organ and a second surface in contact with the stroma;
   the population consisting of a plurality of cell types, the population comprising both the stromal and epithelial tissues of the in vivo tissue structure; the population of cells having a volume described by a first, second and third dimension such that at least one dimension is no greater than 0.45 mm;
   the stromal and epithelial tissues being preserved in the nutrient medium devoid of an internally disposed synthetic support structure and absent a sandwich support structure.

2. The culture according to claim 1, wherein the population of cells maintains the stromal and epithelial tissues as determined by histology; and cell viability as determined by DNA synthesis for at least 48 hours in the absence of serum.

3. The culture according to claim 2, wherein the population of cells retains the stromal and epithelial tissues as determined by histology; and cell viability as determined by DNA synthesis for at least 7 days in the absence of serum.

4. The culture according to claim 2, wherein the first dimension is not greater than the second dimension and smaller than the third dimension, the first dimension being measured in a direction that is substantially parallel with the exterior surface.

5. The culture according to claim 4, wherein the organ is skin, the epithelial tissue is epidermis and the stroma is dermis.

6. The culture according to claim 5, wherein the epidermis contains at least one invagination, such that the cells lining the invagination secrete compositions selected from the group consisting of keratin, sebum and sweat.

7. The culture according to claim 6, wherein the invagination is a hair follicle.

8. The culture according to claim 2, wherein the organ is gut-derived.

9. A The culture according to claim 8, wherein the gut-derived tissue is selected from lung, duodenum, esophagus, intestine, colon, liver and pancreas.

10. The culture according to claim 8, wherein the gut-derived organ is liver and the epithelium is hepatic epithelium and the stroma is hepatic stroma.

11. The culture according to claim 8, wherein the gut-derived organ is pancreas.

12. The culture according to claim 1, wherein the organ is selected from the group consisting of bladder, cornea, breast and gut-derived tissue.

13. The culture according to claim 1, wherein the sum of the inverses of the two smallest dimensions is at least 2.66 mm$^{-1}$.

14. The culture according to claim 1, wherein the sum of the inverses of the two smallest dimensions is at least 3.58 mm$^{-1}$.

15. A micro-organ culture, comprising:
   (i) a nutrient medium in a culture vessel; and
   (ii) a population of non-fetal animal cells disposed in the nutrient medium for at least 24 hours, wherein the population of cells is derived from an organ, the organ having an in vivo tissue structure including an epithelial tissue and an adjacent stroma, wherein the epithelial tissue has a first surface corresponding to an exterior surface of the organ and a second surface in contact with the stroma;

the population consisting of a plurality of cell types, the population comprising both the stromal and epithelial tissues of the in vivo tissue structure; the population of cells having a volume, described by a first, second and third dimension, the first dimension being not greater than the second dimension and smaller than the third dimension, the first dimension corresponding to a plane that is substantially parallel with the exterior surface of the organ, and the first dimension having a size that is no greater than 0.45 mm.

16. The culture according to claim 15, wherein the population of cells is disposed within a nutrient medium in the absence of serum such that the population of cells maintains the stromal and epithelial tissues as determined by histology; and cell viability as determined by DNA synthesis for at least 48 hours.

17. A micro-organ culture, comprising:
(i) a nutrient medium in a culture vessel, the vessel having therein an oxygen concentration not substantially greater than that in the atmosphere; and
(ii) a population of non-fetal animal cells derived from a gut-derived organ, the organ having an in vivo tissue structure including an epithelial tissue and an adjacent stroma, wherein the epithelial tissue has a first surface corresponding to an exterior surface of the organ and a second surface in contact with the stroma;

the population consisting of a plurality of cell types, the population comprising both stromal and epithelial tissues of the in vivo tissue structure; the population of cells having a volume defined by a first, second and third dimension, such that the first dimension is not greater than the second dimension and smaller than the third dimension wherein the first dimension is no greater than 0.45 mm; and the stromal and epithelial tissues being preserved in the nutrient medium devoid of an internally disposed synthetic support structure and absent a sandwich support structure.

18. The culture according to claim 17, wherein the population of cells is disposed within a culture medium in the absence of serum such that the population of cells retains the stromal and epithelial tissues as determined by histology; and cell viability as determined by DNA synthesis for at least 48 hours.

19. A method of making a micro-organ culture, comprising:
(a) providing a nutrient medium in a culture vessel, the vessel having therein an oxygen concentration not substantially greater than that in the atmosphere; and
(b) obtaining a population of non-fetal animal cells, wherein the population is derived form an organ, the organ having an in vivo tissue structure including an epithelial tissue and an adjacent stroma, wherein the epithelial tissue has a first surface corresponding to an exterior surface of the organ and a second surface in contact with stroma;

the population consisting of a plurality of cell types, the population comprising both the stromal and epithelial tissues of the in vivo tissue structure; the population of cells having a volume described by a first, second and third dimension such that at least one dimension is no greater than 0.45 mm; the population of cells being devoid of an internally disposed synthetic support structure and absent a sandwich support structure;

(c) placing the population of cells in the nutrient medium for greater than 24 hours, and preserving the stromal and epithelial tissues of the in vivo tissue structure.

20. A method according to claim 19, wherein the organ is a gut-derived organ.

* * * * *